(12) United States Patent
Foster

(10) Patent No.: US 8,372,262 B2
(45) Date of Patent: Feb. 12, 2013

(54) SIMULTANEOUS DETERMINATION OF CHLORINE AND CHLORATE IN SODIUM HYPOCHLORITE

(75) Inventor: Kevin Anthony Foster, Kent (GB)

(73) Assignee: Siemens Industry, Inc., Alpharetta, GA (US)

(*) Notice: Subject to any disclaimer, the term of this patent is extended or adjusted under 35 U.S.C. 154(b) by 261 days.

(21) Appl. No.: 12/893,860

(22) Filed: Sep. 29, 2010

(65) Prior Publication Data
US 2011/0198239 A1 Aug. 18, 2011

Related U.S. Application Data

(60) Provisional application No. 61/305,685, filed on Feb. 18, 2010.

(51) Int. Cl.
G01N 27/44 (2006.01)
G01N 27/28 (2006.01)
C02F 1/00 (2006.01)

(52) U.S. Cl. ............ 205/778.5; 210/739; 210/749; 210/143

(58) Field of Classification Search ........ 205/778.5; 204/405; 210/739, 749, 96.1, 143
See application file for complete search history.

(56) References Cited

U.S. PATENT DOCUMENTS

| 4,159,929 | A | 7/1979 | Grotheer |
| 5,798,271 | A | 8/1998 | Godec et al. |
| 5,948,236 | A | 9/1999 | Lipsztajn |
| 6,472,223 | B1 | 10/2002 | Stannard et al. |
| 2002/0108911 | A1* | 8/2002 | Xiong et al. ........ 210/739 |

FOREIGN PATENT DOCUMENTS

GB 2312853 * 11/1997

OTHER PUBLICATIONS

Siemes Micro/2000 Mieasurement Module specification, 2009.*
Powell article (A titration method for measuring chlorate ion in concentrated bleach solutions, 2010).*

* cited by examiner

Primary Examiner — J. Christopher Ball
Assistant Examiner — Jennifer Dieterle

(57) ABSTRACT

A process for the simultaneous determination of chlorine and chlorate in sodium hypochlorite. First and second streams of sodium hypochlorite are provided. The first stream is treated to generate iodine indicative of chlorine. The second stream is treated to generate iodine indicative of chlorine and chlorate. The iodine of the first stream is subjected to an amperometric measuring cell to generate a first current proportional to a chlorine concentration of the first stream. The iodine of the second stream is subjected to an amperometric measuring cell to generate a second current proportional to the chlorine and chlorate concentration in the second stream. The first current is subtracted from the second current to determine an amount of chlorate.

16 Claims, 2 Drawing Sheets

SIMULTANEOUS DETERMINATION OF CHLORINE AND CHLORATE IN SODIUM HYPOCHLORITE

CROSS REFERENCE TO RELATED APPLICATION

This application claims priority under 35 U.S.C. §119(e) to U.S. Provisional Application Ser. No. 61/305,685 filed on Feb. 18, 2010 entitled SIMULTANEOUS DETERMINATION OF CHLORINE AND CHLORATE IN SODIUM HYPOCHLORITE which is incorporated by reference in its entirety for all purposes.

FIELD OF THE INVENTION

This invention relates to detection of chlorate, and more particularly, to the simultaneous determination of chlorine and chlorate in sodium hypochlorite produced by the electrolysis of brine by using a three electrode amperometric measurement.

BACKGROUND OF THE INVENTION

Sodium hypochlorite is a common source of chlorine used for disinfection of drinking water. Low strength solutions of sodium hypochlorite may be produced on site by the electrolysis of brine (NaCl) solutions (less than 1% available chlorine).

$$2Cl^- \rightarrow Cl_2 + 2e^- \text{ Anode}$$

$$2H_2O + 2e^- \rightarrow H_2 + 2OH^- \text{ Cathode}$$

$$Cl_2 + OH^- \rightarrow OCl^- + Cl^- + H^+ \text{ Overall reaction}$$

The overall reaction produces hypochlorite (OCl⁻) which then combines with sodium from the brine to produce sodium hypochlorite.

Side reactions are possible during the process. In particular, some of the hypochlorite that is produced will be further oxidized at the anode to produce chlorate (ClO3⁻).

$$6OCl^- + 3H_2O \rightarrow 2ClO_3^- + 4Cl^- + 6H^+ + 1.5O_2 + 6e^-$$

Additionally, decomposition due to storage and heat can lead to further chlorate production.

$$2HOCl + OCl^- \rightarrow ClO_3^- + 2Cl^- + 2H^+$$

Recently, chlorate has become a focus in the drinking water industry. In particular, the World Health Organization has issued a guideline which limits chlorate to 0.7 mg/l. In order to keep within this limit, users of sodium hypochlorite are increasingly aware of the importance of knowing the initial levels of chlorate.

SUMMARY OF THE INVENTION

A method for determining an amount of chlorate in hypochlorite is disclosed. The method includes treating first and second streams of sodium hypochlorite to generate iodine indicative of chlorine in the first stream and iodine indicative of chlorine and chlorate in the second stream, respectively. The method further includes subjecting the iodine of the first stream to an amperometric measuring cell to generate a first current proportional to a chlorine concentration of the first stream. The iodine of the second stream is simultaneously subjected to an amperometric measuring cell to generate a second current proportional to the chlorine and chlorate concentration in the second stream. The first current is then subtracted from the said second current to determine an amount of chlorate.

DETAILED DESCRIPTION OF THE INVENTION

Figure 1:
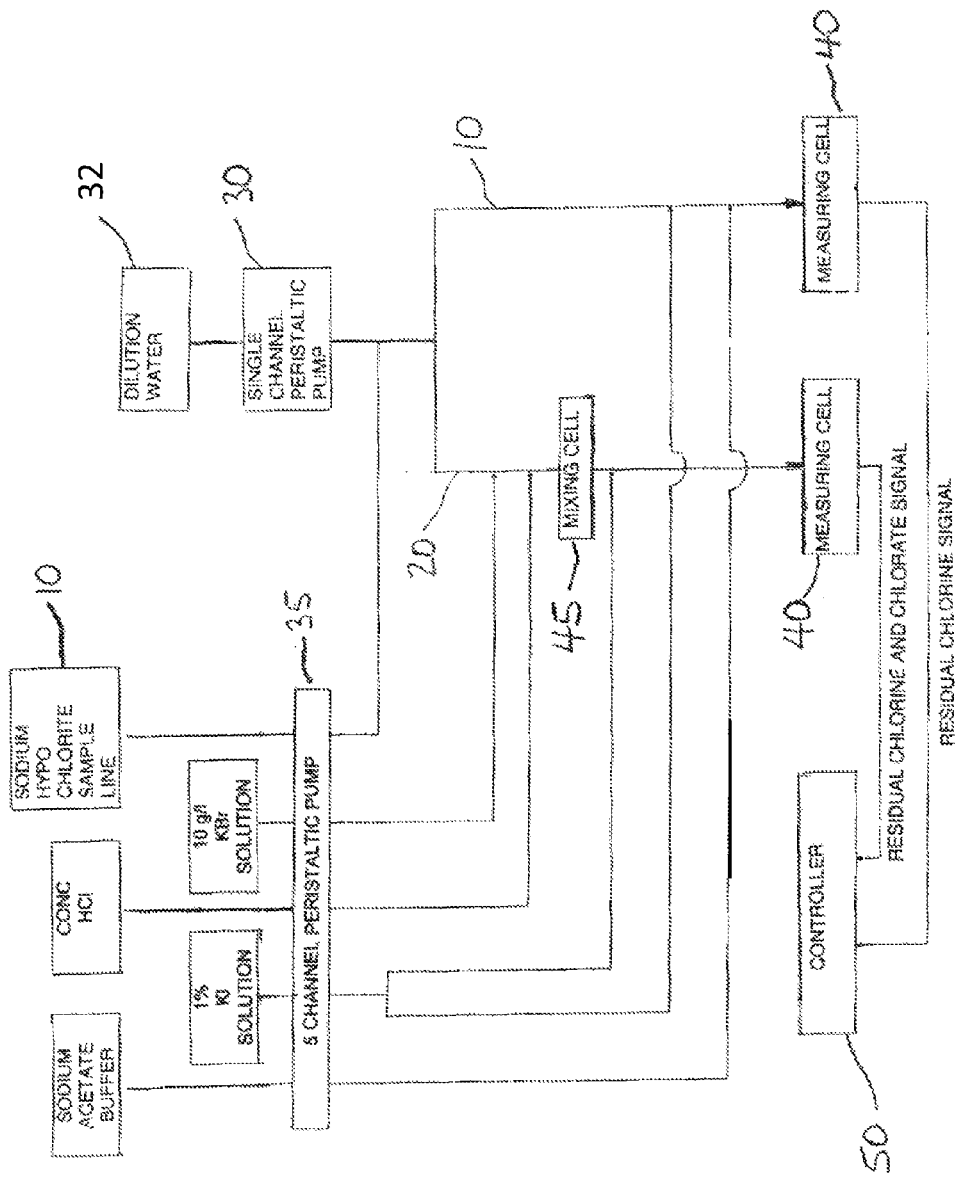
FIG. 1 is a schematic representation of the present invention.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass direct and indirect mountings, connections, supports, and couplings. Further, "connected" and "coupled" are not restricted to physical or mechanical connections or couplings. In the description below, like reference numerals and labels are used to describe the same, similar or corresponding parts in the several views of FIGS. 1 and 2.

Referring to FIG. 1, a schematic representation of the present invention is shown. Sodium hypochlorite from sodium hypochlorite sample line 10 is divided into first 10 and second 20 sodium hypochlorite sample streams. The first 10 and second 20 streams are controlled by a first pump 30, which may be a single channel peristaltic pump. The first 10 and second 20 streams are each diluted with water 32 to reduce the hypochlorite concentration to less than 100 mg/l and the chlorate concentration to less than 10 mg/l.

The first stream 10 is treated with reagents such as sodium acetate buffer (CH3COONa) delivered by means of 50% acetic acid and potassium iodide (KI). The sodium acetate buffer and potassium iodide reagents are controlled by a second pump 35, which may be a five channel peristaltic pump. For example, an approximately 1% potassium iodide solution may be used. Under theses acidic conditions, the chlorine in the hypochlorite oxidizes the iodide to iodine (I2). The second stream 20 is treated with reagents such as potassium bromide (KBr), hydrochloric acid (HCl) and potassium iodide (KI) which are also controlled by the second pump 35. For example, an approximately 10 g/l potassium bromide solution may be used. Under these conditions the hypochlorite/chlorate oxidizes the iodide to iodine.

The first 10 and second 20 streams are each fed to an amperometric measuring cell 40 which includes an impeller and an amperometric probe having three electrodes. By way of example, a commercially available analyzer such as the Micro/2000® Measurement Module sold by Siemens may be used. Both analyzers may be controlled by multi channel controller 50 such as the MFC analyzer/controller sold by Siemens. The working electrode of the probe is maintained at between approximately 200 and 300 mv by a potentiostat circuit or similar device. At this potential, the iodine is reduced to iodide and a current proportional to the iodine concentration is passed between the working and counter electrode.

In particular, with respect to the first stream 10, the chlorine reacts with the iodide to produce iodine. This is then reduced at the working electrode of the three electrode cell 40 to produce a current (μA) which is proportional to the iodine, and hence chlorine, concentration.

Cl2+2KI-→I2+2KCl Oxidation of Iodide by chlorine

I2+2e-→2I- Reduction current measured at working electrode

The first stream 10 develops a current of approximately 5 μA/mg/l of iodine which is proportional to the chlorine concentration in the hypochlorite. The reaction for the second stream 20 is similar in that ultimately all of the chlorine/chlorate reacts with the iodide to produce iodine. The second stream 20 develops a current of approximately 5 μA/mg/l of iodine which is proportional to the chlorine and the chlorate concentration in the hypochlorite.

In accordance with the present invention, the current associated with the first stream 10 is subtracted from the current associated with second stream 10. The difference between the two streams is due to chlorate formation. In addition, the two currents are processed to determine chlorine in g/l and chlorate in mg/l in the hypochlorite. The process can then determine the maximum allowable chlorine dosage for a maximum chlorate residual of 0.7 mg/l.

Measurement during the process is continuous. A lag or retention time of approximately 10 minutes is introduced to ensure complete reaction of the chlorate with the hydrochloric acid and the potassium bromide in a mixing cell 45. The controller is programmed to subtract the two streams. In addition, the controller may be programmed to delay the chlorine only signal by approximately 10 minutes to provide a correct point for subtraction. The process requires less than approximately 1 ml/min of sample and typically requires approximately 2.5 liters of each reagent per month.

Figure 2:
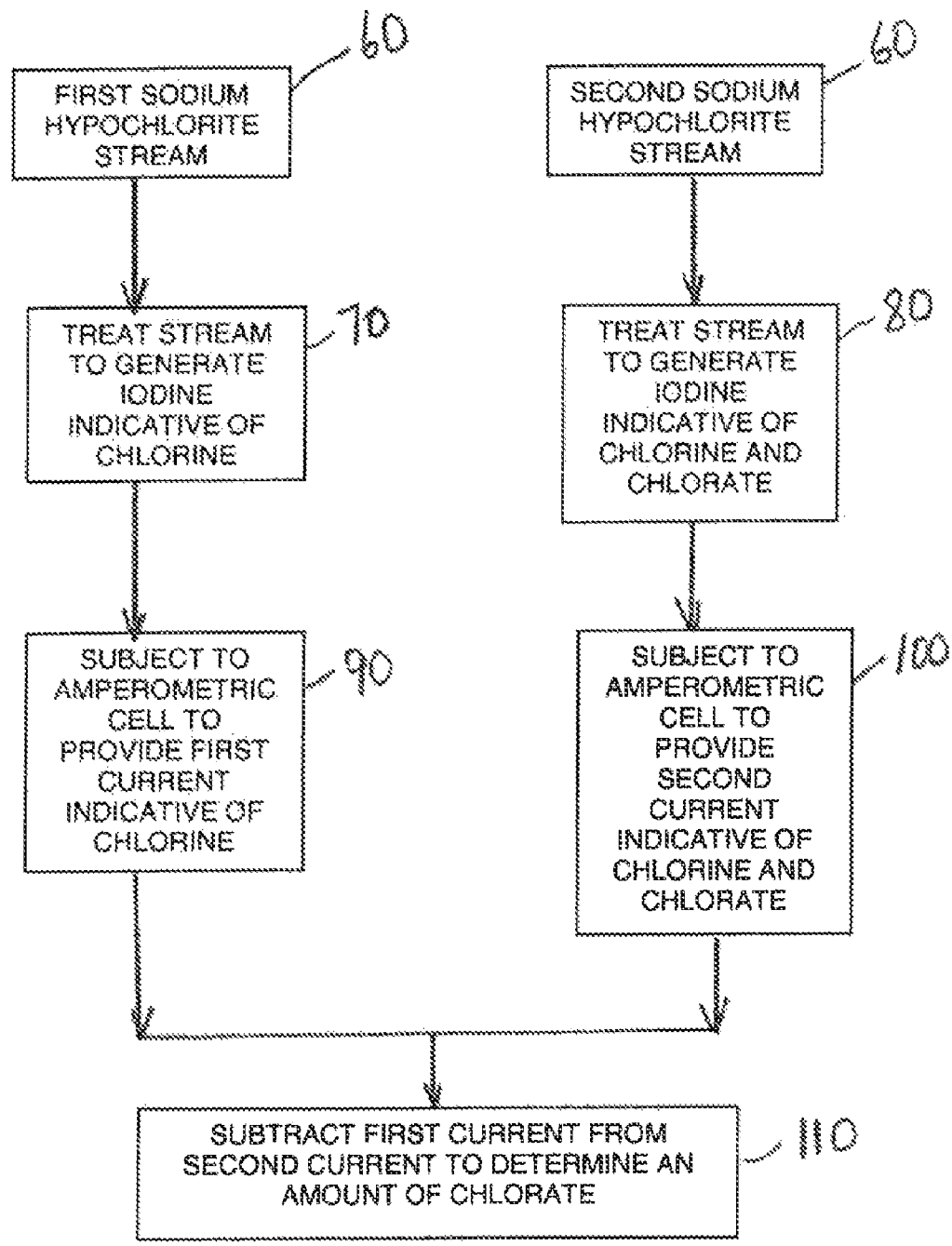
FIG. 2 depicts a process for the simultaneous determination of chlorine and chlorate in hypochlorite.

Referring to FIG. 2, a process for the simultaneous determination of chlorine and chlorate in sodium hypochlorite is shown. In step 60, first and second streams of sodium hypochlorite are provided. The first stream is treated to generate iodine indicative of chlorine at step 70. The second stream is treated to generate iodine indicative of chlorine and chlorate at step 80. At step 90, the iodine of the first stream is subjected to an amperometric measuring cell to generate a first current proportional to a chlorine concentration of the first stream. At step 100, which occurs relatively simultaneously with step 90, the iodine of the second stream is subjected to an amperometric measuring cell to generate a second current proportional to the chlorine and chlorate concentration in the second stream. The first current is subtracted from the second current to determine an amount of chlorate at step 110.

While the invention has been described in conjunction with specific embodiments, it is evident that many alternatives, modifications, permutations and variations will become apparent to those skilled in the art in light of the foregoing description. Accordingly, it is intended that the present invention embrace all such alternatives, modifications and variations.

What is claimed is:

1. A method for determining an amount of chlorate in sodium hypochlorite comprising the steps of:
providing first and second streams of the sodium hypochlorite;
treating said first stream to generate iodine indicative of chlorine in said first stream;
treating said second stream to generate iodine indicative of chlorine and chlorate in said second stream;
subjecting said iodine of said first stream to a first amperometric measuring cell to generate a first current proportional to a chlorine concentration of said first stream;
subjecting said iodine of said second stream to a second amperometric measuring cell to generate a second current proportional to a chlorine and chlorate concentration in the second stream;
and subtracting said first current from said second current to determine the amount of chlorate in the sodium hypochlorite.

2. The method according to claim 1 wherein said first and second streams are diluted with water to reduce a hypochlorite concentration to less than approximately 100 mg/l and a chlorate concentration to less than approximately 10 mg/l.

3. The method according to claim 1 wherein said first current is approximately 5 μA/mg/l of iodine.

4. The method according to claim 1 wherein said second current is approximately 5 μA/mg/l of iodine.

5. The method according to claim 1 further comprising delaying a signal representing the first current by about 10 minutes.

6. The method according to claim 1 further comprising maintaining a working electrode at between approximately 200 and 300 mv.

7. The method of claim 1, further comprising determining a maximum allowable chlorine dosage for a maximum chlorate residual of about 0.7 mg/l.

8. The method according to claim 1 wherein said first stream is treated with a sodium acetate buffer and potassium iodide.

9. The method according to claim 8 wherein an approximately 1% solution of potassium iodide is used.

10. The method according to claim 1 wherein said second stream is treated with potassium bromide, hydrochloric acid and potassium iodide.

11. The method according to claim 10 wherein an approximately 10 g/l solution of potassium bromide is used.

12. The method according to claim 1 further including the step of providing a retention time to ensure complete reaction of said chlorate.

13. The method according to claim 12 wherein said retention time is approximately 10 minutes.

14. The method according to claim 1 wherein the amount of chlorate in the sodium hypochlorite is measured continuously.

15. The method according to claim 14 wherein less than approximately 1 ml/min of the sodium hypochlorite is required.

16. The method according to claim 14 wherein approximately 2.5 liters of each reagent is required per month.

* * * * *